United States Patent [19]

Massonneau et al.

[11] Patent Number: 4,925,952

[45] Date of Patent: May 15, 1990

[54] PROCESS FOR PREPARING 1-HYDROXYALKYL-5-NITROIMIDAZOLES

[75] Inventors: Viviane Massonneau; Michel Mulhauser, both of Ecully; Albert Buforn, Lyons; Bernadette Mandard-Cazin, Alfortville, all of France

[73] Assignee: Rhone-Poulenc Sante, Antony, France

[21] Appl. No.: 296,710

[22] Filed: Jan. 13, 1989

[30] Foreign Application Priority Data

Jan. 15, 1988 [FR] France ............................ 88 00415

[51] Int. Cl.$^5$ .................. C07D 233/94; C07D 405/06
[52] U.S. Cl. .................................. 548/338; 548/336; 548/339; 548/340
[58] Field of Search ................ 548/338, 336, 339, 340

[56] References Cited

U.S. PATENT DOCUMENTS 3,178,446  4/1965  Sannicolo ............................ 548/338
3,743,653  7/1973  Marburg .............................. 548/340

FOREIGN PATENT DOCUMENTS 3270       4/1965  France .
1079271    8/1967  United Kingdom .

OTHER PUBLICATIONS

*Chemical Abstracts*, 77:139490t, (1972), [D. Tomalia, et al., *J. Heterocycl. Chem.*, 1972, 9(4), pp. 891–894].

Primary Examiner—Richard A. Schwartz
Attorney, Agent, or Firm—Stevens, Davis, Miller & Mosher

[57] ABSTRACT

Process for preparing 1-(hydroxyalkyl)nitroimidazoles of formula:

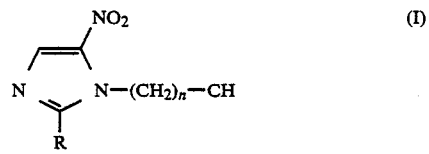

which comprises reacting an alkylene sulphate of formula:

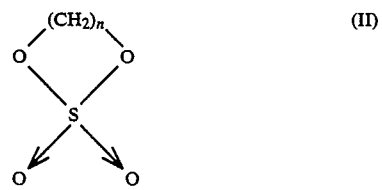

with an imidazole derivative of formula:

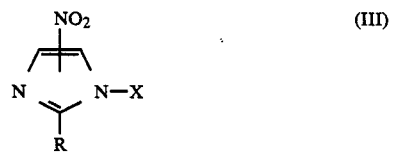

followed by hydrolyzing or alcoholyzing the product obtained. In the formulae (I) and (II), n is 2 or 3; in the formulae (I) and (III), R denotes hydrogen or hydrocarbon radical; and in the formula (III), X denotes hydrogen or a radical that can be removed by hydrolysis or alcoholysis.

7 Claims, No Drawings

PROCESS FOR PREPARING 1-HYDROXYALKYL-5-NITROIMIDAZOLES

The present invention relates to a new process for preparing 1-hydroxyalkyl-5-nitroimidazole.

Among imidazole derivatives, 1-hydroxyethyl-2-methyl-5-nitroimidazole (or metronidazole), 1-(2-hydroxypropyl)-2-methyl-5-nitroimidazole (or secnidazole) and 1-(3-hydroxypropyl)-2-methyl-5-nitroimidazole (or terndazole) are of particular importance on account of their noteworthy therapeutic properties.

It is known to prepare metronidazole by the action of an excess of ethylene oxide on 2-methyl-4(or 5)-nitroimidazole under the conditions described in French Patent 1,379,915. However, the yields are not satisfactory.

It is known to prepare 2-(4-fluorophenyl)-1-hydroxyethyl-5-nitroimidazole by the action of ethylene sulphate on 2-(4-fluorophenyl)-4(or 5)-nitroimidazole according to the process described in U.S. Pat. No. 3,743,653. However, in this case, the yield is less than 10%.

According to the present invention, it has now been found that 1-(hydroxyalkyl)nitoimidazoles of formula:

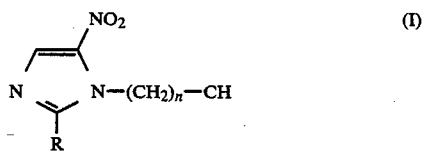

in which R denotes hydrogen, alkyl of 1 to 4 carbon atoms, or alkenyl of 2 to 4 carbon atoms, the said alkyl and alkenyl being unsubstituted or substituted by one or more identical or different radicals chosen from phenyl, phenoxy, and 5- or 6-membered oxygen-containing heterocyclic radicals, or alternatively R denotes aryl of 6 to 10 carbon atoms unsubstituted or substituted by one or more identical or different substituents chosen from halogen, alkyl of 1 to 4 carbon atoms, alkoxy of 1 to 4 carbon atoms, phenyl, phenoxy and nitro, or alternatively R denotes cycloalkyl of 5 or 6 carbon atoms; the aforesaid phenyl, phenoxy and heterocyclic radicals being unsubstituted or substituted by one or more identical or different substitutents chosen from halogen, alkyl of 1 to 4 carbon atoms, alkoxy of 1 to 4 carbon atoms, phenyl, phenoxy or nitro; and n is 2 or 3 and one of the carbon atoms of the alkylene chain —$(CH_2)_n$— can be substituted by methyl, may be obtained in good yield by a process which comprises reacting an alkylene sulphate of formula:

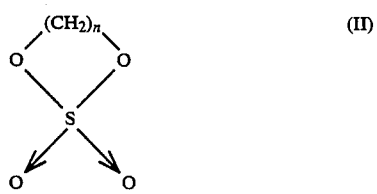

in which n is 2 or 3 and one of the carbon atoms of the alkylene chain —$(CH_2)_n$— can be substitutedby methyl with a nitroimidazole of formula:

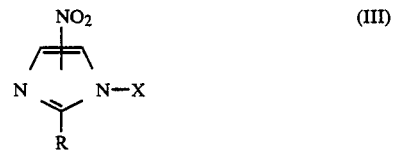

in which R is defined as above and X denotes hydrogen or a radical that can be removed by hydrolysis or alcoholysis, such as a hydroxymethyl radical, an alkoxymethyl radical in which the alkyl portion contains 1 to 4 carbon atoms, an acyloxymethyl radical in which the acyl portion contains 1 to 4 carbon atoms, an allylic ethylenic radical such as allyl, or an arylmethyl such as benzyl, hydrolysing or alcoholysing the product obtained, and isolating the 1-(hydroxyalkyl)nitroimidazole.

More especially, the present invention provides a process for preparing 1-hydroxyethyl-2-methyl-5-nitroimidazole, 1-(2-hydroxypropyl)-2-methyl-5-nitroimidazole, 1-(3-hydroxypropyl)-2-methyl-5-nitroimidazole and 1-hydroxyethyl-5-nitroimidazole.

The condensation of the alkylene sulphate of general formula (II) with the imidazole derivative of general formula (III) is performed at a temperature from 60° to 120° C.; and optionally in the presence of an organic solvent chosen from esters such as methylacetate, ethylacetate, or glycol diacetate, ketones such as methyl isobutyl ketone, ethers such as methyl tert-butyl ether, aliphatic or aromatic halogenated or unhalogenated hydrocarbons, such as benzene, toluene, xylene, chloroform, dichloromethane or chlorobenzene, or nitriles such as acetonitrile.

The condensation product which precipitates may be dissolved:

either in an aqueous solution of a strong mineral acid such as, e.g., sulphuric acid or hydrochloric acid
or in an alcohol such as, e.g., methanol or ethanol.

When the condensation product is dissolved in aqueous acid, the 1-(hydroxyalkyl)nitroimidazole is extracted according to the usual techniques after the pH of the reaction medium has been adjusted to be in the region of 10.

When the condensation product is dissolved in an alcohol, the 1-(hydroxyalkyl)nitroimidazole is isolated according to the usual techniques without prior treatment of the reaction mixture.

When carrying out the process, it is not necessary to isolate the intermediate condensation product, and it is possible for the hydrolysis or alcoholysis to be performed sequentially in the same apparatus.

The alkylene sulphate of formula (II), and more especially ethylene sulphate, may be obtained under the conditions described in German Patent 1,029,382.

The nitrioimdazole derivative of formula (III) may be prepared under the conditions described in British Patent 1,026,631.

The examples which follow show how the invention may be put into practice.

EXAMPLE 1

1-Acetoxymethyl-2-methyl-4-nitroiumidazole (2 g; 0.01 mole), ethylene sulphate (2.6 g; 0.02 mole) and ethylene glycol diacetate (5 cc) are introduced into a round-bottomed flask equipped with a stirrer, and the mixture is then heated for 4 hours to 80° C. The white precipitate which appears is separated off by filtration and washed twice with methyl acetate (5 cc). After drying, a white solid (3.4 g) is obtained.

Analysis of the filtrate by high performance liquid chromatography (HPLC) shows:

that it contains 1-acetoxymethyl-2-methyl-4-nitroimidazole (98.6 mg). The degree of conversion of 1-acetoxymethyl-2-methyl-4-nitroimidazole is 95%;

that the mixture of imidazole derivatives consists of 1-acetoxymethyl-2-methyl-4-nitroimidazole (98.5%) and 2-methyl-4(or 5)-nitroimidazole (0.5%).

1.705 g of the white solid obtained above is added to a solution of concentrated sulphuric acid (1 cc) in water (5 cc). The solution obtained is heated for 10 minutes to 80° C. and the pH is the adjusted to pH 10 by adding sodium hydroxide. The precipitate which forms is separated off by filtration and then dried. A product (0.685 g) containing metronidazole (95%) is thereby obtained (assay by HPLC with internal calibration).

The yield of metronidazole isolated is 76.1% relative to the 1-acetoxymethyl-2-methyl-4-nitroimidazole introduced.

Analysis of the filtrate shows that it contains metronidazole (69.6 mg) and 2-methyl-4(or 5)-nitroimidazole (11.3 mg). The overall yield of metronidazole is 84.2% relative to the 1-acetoxymethyl-2-methyl-4-nitroimidazole introduced and is 89% relative to the 1-acetoxymethyl-2-methyl-4-nitroimidazole converted.

EXAMPLE 2

The procedure is as in Example 1, but using 1-acetoxymethyl-2-methyl-4-nitroimidazole (2 g; 0.01 mole) and ethylene sulphate (1.3 g; 0.01 mole). After heating for 4 hours to 80° C., the precipitate formed is separated off by filtration and dried. A white product (2.85 g) is thereby obtained.

Analysis of the filtrate by HPLC, after adjustment of the pH to 10, shows that is contains 2-methyl-4(or 5)-nitroimidazole (315 mg). The degree of conersion of 1-acetoxymethyl-2-methyl-4-nitroimidazole is 75%.

The mixture of imidazole derivatives present in the solution consists of 2-methyl-4(or 5)-nitroimidazole (96%) and metronidazole (1.5%) (assay by HPLC with internal standardization).

0.57 g of the white product obtained above is added to ethanol (5 cc). The mixture obtained is heated under reflux of the ethanol for 4 hours until a homogeneous solution is obtained.

After dilution of the reaction mixture, metronidazole (201 mg) is assayed.

The yield of metronidazole is 59% relative to the 1-acetoxymethyl-2-methyl-4-nitroimidazole introduced and is 81% relative to the 1-acetoxymethyl-2-methyl-4-nitroimidazole converted.

The mixture of imidazole derivative present in the solution consists of metronidazole (94.8%) and 2-methyl-4(or 5)-nitroimidazole (4.1%).

EXAMPLE 3

0.57 g of the white product in Example 2 is added to a solution of concentrated sulphuric acid (0.2 cc) in water (2 cc). The solution obtained is heated for 1 hour 30 minutes to 80° C., and the pH is adjusted to pH 10 by adding sodium hydroxide.

In the solution obtained, metronidazole (260 mg) is assayed by HPLC.

The yield of metronidazole is 71.6% relative to the 1-acetoxymethyl-2-methyl-4-nitroimidazole introduced and is 95% relative to the 1-acetoxymethyl-2-methyl-4-nitroimidazole converted.

The mixture of imidazole derivatives present in the solution consists of metronidazole (92.8%) and 2-methyl-4(or 5)-nitroiumidazole (2.5%).

EXAMPLE 4

The procedure is as in Example 2, using 1-acetoxymethyl-2-methyl-4-nitroimidazole (0.603 g; 0.003 mole) and ethylene sulphate (0.372 g; 0.003 mole) in chloroform (3 cc). The mixture is heated for 5 hours to the boiling point of the chloroform. The precipitate which has appeared is separated off by filtration and washed with chloroform. After drying, a white solid (0.56 g) is obtained.

In the filtrate, 1-acetoxymethyl-2-methyl-4-nitroimidazole (270 mg) and 2-methyl-4(or 5)-nitroimidazole (7.35 mg) are assayed by HPLC with external calibration.

The mixture of imidazole derivatives in the filtrate consists of 1-acetoxymethyl-2-methyl-4-nitroimidazole (94.6%) and 2-methyl-4(or 5)-nitroimidazole (3.4%).

The white solid obtained above (0.56 g) is added to ethanol (6 cc). The mixture is heated for 4 hours to the refluxing temperature of the ethanol. After dilution of the reaction mixture, metronidazole (193 mg) and 2-methyl-4(or 5)-nitroimidazole (16.5 mg) are assayed by HPLC.

The yield of metronidazole is 38% relative to the 1-acetoxymethyl-2-methyl-4-nitroimidazole introduced and is 76% relative to the 1-acetoxymethyl-2-methyl-4-nitroimidazole converted.

The degree of conversion of 1-acetoxymethyl-2-methyl-4-nitroimidazole is 49%.

The mixture of imidazole derivatives in the solution consists of metronidazole (89.1%) and 2-methyl-4(or 5)-nitroimidazole (9.6%).

EXAMPLE 5

The procedure is as in Example 2, but using 1-acetoxymethyl-2-methyl-4-nitroimidazole (0.208 g; 0.001 mole) and ethylene sulphate (0.156 g; 0.0012 mole) in xylene (2 cc). The mixture is heated to 80° C. for 4 hours. Ethanol (3 cc) is then added and the mixture is heated under reflux for 3 hours. In the solution thereby obtained, metronidazole (103 mg) and 2-methyl-4(or 5)-nitroimidazole (44 mg) are assayed.

The mixture of imidazole derivatives in the solution consists of metronidazole (65.2%) and 2-methyl-4(or 5)-nitroimidazole (33.5%).

The degree of conversion of 1-acetoxymethyl-2-methyl-4-nitroimidazole is 67%.

The yield of metronidazole is 58% relative to the 1-acetoxymethyl-2-methyl-4-nitroimidazole introduced and is 87% relative to the 1-acetoxymethyl-2-methyl-4-nitroimidazole converted.

EXAMPLE 6

The procedure is as in Example 5, using methyl isobutyl ketone (2 cc) as solvent. After 4 hours' heating at 80° C., a gummy precipitate appears. Ethanol (3 cc) is added and the mixture is heated under reflux for 4 hours.

In the solution obtained, metronidazole (46.8 mg) and 2-methyl-4(or 5)-nitroimidazole (94.9 mg) are assayed.

The degree of conversion of 1-acetoxymethyl-2-methyl-4-nitroimidazole is 28%.

The yield of metronidazole is 26% relative to the 1-acetoxymethyl-2-methyl-4-nitroimidazole introduced and is 93.5% relative to the 1-acetoxymethyl-2-methyl-4-nitroimidazole converted.

EXAMPLE 7

The procedure is as in Example 5, but using acetonitrile (2 cc) as solvent. The mixture is heated to 80° C. for 4 hours. A white precipitate appears. Ethanol (3 cc) is added and the mixture is then heated under reflux for 4 hours.

In the solution, metronidazole (57.8 mg), 1-acetoxymethyl-2-methyl-4-nitroimidazole (30.2 mg) and 2-methyl-4(or 5)-nitroimidazole (58.3 mg) are assayed.

The degree of conversion of 1-acetoxymethyl-2-methyl-4-nitroimidazole is 41%.

The yield of metronidazole is 32.5% relative to the 1-acetoxymethyl-2-methyl-4-nitroimidazole introduced and is 79% relative to the 1-aceotxymethyl-2-methyl-4-nitroimidazole converted.

EXAMPLE 8

1-Acetoxymethyl-2-methyl-4-nitroimidazole (0.573 g; 0.00288 mole) and ethylene sulphate (0.4 g; 0.00322 mole) are introduced into a round-bottomed flask equipped with a stirrer. The reaction mixture is heated for 1 hour to 90° C. Ethanol (5 cc) is then added, and the mixture is then heated under reflux for 4 hours.

After dilution, metronidazole (393 mg) and 2-methyl-4(or 5)-nitroimidazole (23.7 mg) are assayed in the solution obtained.

The mixture of imidazole derivatives in the solution consists of 2-methyl-4(or 5)-nitroimidazole (6.9%) and metronidazole (91%).

The degree of conversion of 1-acetoxymethyl-2-methyl-4-nitroimidazole is 93.5%.

The yield of metronidazole is 80% relative to the 1-acetoxymethyl-2-methyl-4-nitroimidazole introduced and is 85.3% relative to the 1-acetoxymethyl-2-methyl-4-nitroimidazole converted.

EXAMPLE 9

2-Methyl-4(or 5)-nitroimidazole (130 mg; 0.001 mole), ethylene sulphate (130 mg; 0.001 mole) and glycol diacetate (0.53 cc) are introduced into a round-bottomed flask equipped with a stirrer. The mixture is heated to 120° C. for 1 hour. A precipitate forms. Sulphuric acid (d=1.83) (30 microliters) is added and the reaction mixture is then heated for 4 hours to 120° C. After cooling, a solution of concentrated sulphuric acid (0.2 cc) in water (1 cc) is added. The solution obtained is heated to 80° C. for 1 hour 30 minutes.

After cooling, the reaction mixture is diluted. Metronidazole (70 mg) and 2-methyl-4(or 5)-nitroimidazole (29 mg) are assayed by high performance liquid chromatography (HPLC).

The degree of conversion of 2-methyl-4(or 5)-nitroimidazole is 77%.

The yield of metronidazole is 41% relative to the 2-methyl-4(or 5)-nitroimidazole introduced and 53.2% relative to the 2-methyl-4(or 5)-nitroimidazole converted.

EXAMPLE 10

2-Methyl-4(or 5)-nitroimidazole (131 mg; 0.001 mole), ethylene sulphate (130 mg; 0.001 mole) and xylene (2 cc) are introduced into a round-bottomed flask equipped with a stirrer. The mixture is heated for 4 hours to 80° C. Ethanol (5 cc) is then added and the mixture is heated under reflux for 4 hours.

In the solution obtained, metronidazole (25 mg) and 2-methyl-4(or 5)-nitroimidazole (100 mg) are assayed by HPLC.

The degree of conversion of 2-methyl-4(or 5)-nitroimidazole is 23%.

The yield of metronidazole is 14% relative to the 2-methyl-4(or 5)-nitroimidazole introduced and 60% relative to the 2-methyl-4(or 5)-nitroimidazole converted.

EXAMPLE 11

2-Methyl-4(or 5)-nitroimidazole (130 mg; 0.001 mole) and ethylene sulphate (130 mg: 0.001 mole) are introduced into a round-bottomed flask equipped with a stirrer. The reaction mixture is heated for 4 hours to 90° C. Ethanol (5 cc) is then added and the mixture is thereafter heated under reflux for 4 hours.

After dilution of the reaction mixture, metronidazole (42.4 mg) and 2-methyl-4(or 5)-nitroimidazole (76.2 mg) are assayed by HPLC.

The degree of conversion of 2-methyl-4(or 5)-nitroimidazole is 42%.

The yield of metronidazole is 24% relative to the 2-methyl-4(or 5)-nitroimidazole introduced and 58% relative to the 2-methyl-4(or 5)-nitroimidazole converted.

EXAMPLE 12

1-Acetoxymethyl-2-methyl-4-nitroimidazole (12 g; 0.06 mole), propylene sulphate (10 g: 0.072 mole) and xylene (40 cc) are introduced into a round-bottomed flask equipped with a stirrer.

The reaction mixture is heated to 110° C. for 5 hours. As soon as the heating is started, a gummy precipitate appears. Water (20 cc) and concentrated sulphuric acid (1.5 cc; 0.028 mole) are then added and the mixture is heated under reflux for 4 hours.

The mixture is cooled is 20° C. A separated xylene phase is extracted with water (90 cc). In the combined aqueous phases, secnidazole (4.32 g), 1-(1-hydroxy-2-methylethyl)-2-methyl-5-nitroimidazole (0.33 g) and 2-methyl-4(or 5)-nitroimidazole (3.1 g) are assayed by HPLC.

The degree of conversion of 1-acetoxymethyl-2-methyl-4-nitroimidazole is 59%.

The yield of secnidazole is 39% relative to the 1-acetoxymethyl-2-methyl-4-nitroimidazole introduced and 64% relative to the 1-aceoxymethyl-2-methyl-4-nitroimidazole converted.

EXAMPLE 13

1-Acetoxymethyl-4-nitroimidazole (4.65 g; 0.025 mole), ethylene sulphate (4.16 g; 0.0325 mole) and xylene (30 cc) are introduced into a round-bottomed flask equipped with a stirrer. The mixture is heated for 6 hours to 80° C. Water (30 cc) and concentrated sulphuric acid (2 cc) are then added. The two-phase reaction mixture is heated under reflux for 4 hours.

Assay of the aqueous phase by high performance liquid chromatography (HPLC) with external calibration shows that:

the degree of conversion of 1-acetoxymethyl-4-nitroimidazole is 86%.

the yield of 1-hydroxyethyl-5-nitroimidazole is 73.7% relative to the 1-acetoxymethyl-4-nitroimidazole converted.

EXAMPLE 14

1-Acetoxymethyl-2-methyl-4-nitroimidazole (2 g; 0.01 mole), propylene sulphate (1.8 g; 0.013 mole) and xylene (10 g) are introduced into a round-bottomed flask equipped with a stirrer. The mixture is heated for 6 hours to 100° C. Water (10 cc) and concentrated sulphuric acid (1 cc) are then added. The reaction mixture is heated under reflux for 3 hours.

Assay of the aqueous phase by high performance liquid chromatography (HPLC) with external calibration shows that:
- the degree of conversion of 1-acetoxymethyl-2-methyl-4-nitroimidazole is 43%
- the yield of 1-(3-hydroxypropyl)-2-methyl-5-nitroimidazole is 95% relative to the 1-acetoxymethyl-2-methyl-4-nitroimidazole converted.

What is claimed is:

1. A process for preparing 1-(hydroxyalkyl)nitroimidazoles of formula:

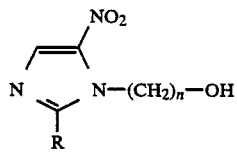

in which R denotes hydrogen, alkyl of 1 to 4 carbon atoms, or alkenyl of 2 to 4 carbon atoms, the said alkyl and alkenyl being unsubstituted or substituted by one or more identical or different radicals chosen from phenyl, phenoxy and 5- or 6-membered oxygen-containing heterocyclic radicals, or alternatively, R denotes aryl of 6 to 10 carbon atoms, unsubstituted or substituted by one or more, identical or different, substituents chosen from halogen, alkyl of 1 to 4 carbon atoms, alkoxy of 1 to 4 carbon atoms, phenyl, phenoxy and nitro, or alternatively, R denotes cycloalkyl of 5 or 6 carbon atoms;

the aforesaid phenyl, phenoxy and heterocyclic radicals being unsubstituted or substituted by one or more, identical or different, substituents chosen from halogen, alkyl of 1 to 4 carbon atoms, alkoxy of 1 to 4 carbon atoms, phenyl, phenoxy or nitro; and n is 2 or 3 and one of the carbon atoms of the alkylene chain $(-CH_2-)_n$ can be substituted by methyl, which comprises reacting an alkylene sulphate of formula:

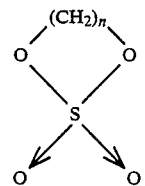

in which n is 2 or 3 and one or the carbon atoms of the alkylene chain $(-CH_2-)_n$ can be substituted by methyl, at 60° to 120° C. with a nitroimidazole of formula:

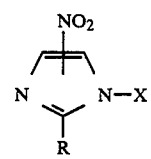

in which R is defined as above and X denotes a radical that can be removed by hydrolysis or alcoholysis; and hydrolysing or alcoholysing the product obtained and isolating the 1-(hydroxyalkyl)nitroimidazole product.

2. A process according to claim 1, wherein the group which can be removed by hydrolysis or alcoholysis is a hydroxymethyl radical, an alkoxymethyl radical in which the alkyl portion contains 1 to 4 carbon atoms, an acyloxymethyl radical in which the acyl portion contains 1 to 4 carbon atoms, an allylic ethylenic radical or an arylmethyl radical.

3. A process according to claim 1, wherein the reaction between the nitroimidazole and alkylene sulphate is performed in an organic solvent chosen from esters, ethers, ketones, aliphatic or aromatic halogenated or unhalogenated hydrocarbons, and nitriles.

4. A process according to claim 3, wherein the solvent is methyl acetate, ethyl acetate, glycol diacetate, methyl tert-butyl ether, methyl isobutyl ketone, chloroform, dichloromethane, benzene, toluene, xylene, chlorobenzene or acetonitrile.

5. A process according to claim 1, wherein the hydrolysis of the condensation product is performed in the presence of sulphuric acid or hydrochloric acid.

6. A process according to claim 1, wherein the alcholysis is performed by heating in the presence of methanol or ethanol.

7. A process according to claim 1, wherein the 1-(hydroxyalkyl)nitroimidazole obtained is metronidazole, secnidazole, ternidazole or 1-hydroxyethyl-5-nitroimidazole.

* * * * *